United States Patent [19]

Bashaw

[11] 4,297,994
[45] Nov. 3, 1981

[54] CERVICAL IMMOBILIZER

[76] Inventor: Robert W. Bashaw, 7008 Creel Dr., Pensacola, Fla. 32506

[21] Appl. No.: 97,879

[22] Filed: Nov. 27, 1979

[51] Int. Cl.³ ............................................ A61F 13/00
[52] U.S. Cl. ................................................... 128/133
[58] Field of Search ............. 128/75, 76, 87 R, 87 B, 128/83, 132 R, 133, 134

[56] References Cited

U.S. PATENT DOCUMENTS

| | | | |
|---|---|---|---|
| 3,650,523 | 3/1972 | Darby, Jr. ........................... | 128/134 |
| 3,724,453 | 4/1973 | Dixon et al. ........................ | 128/134 |
| 3,737,923 | 6/1973 | Prolo ................................. | 128/134 X |
| 3,868,951 | 3/1975 | Albrecht ............................ | 128/75 |
| 4,141,368 | 2/1979 | Meyer .............................. | 128/87 B |
| 4,182,322 | 1/1980 | Miller ................................. | 128/133 |

*Primary Examiner*—John D. Yasko
*Attorney, Agent, or Firm*—Armstrong, Nikaido, Marmelstein & Kubovcik

[57] ABSTRACT

A method and apparatus for immobilizing a head and neck of a patient on a support comprising sliding a base between the patient and the support or attaching device to support prior—until the center portion of a U-shaped headband affixed to the base abuts the top of the head of the patient, attaching the base to the support, positioning a first cushion attached to an end portion of the headband next to, and in contact with, one side of the head of the patient, securing the first cushion in position to the base with a first fastener, positioning a second cushion attached to the other end portion of the headband next to, and in contact with, the other side of the head, securing the second cushion in position to the base with a second fastener such that the central portion of the U-shaped headband is snug against the top of the head, and securing a chin strap cradling the chin of the patient by attaching the strap to the end portion of the U-shaped headband with a third fastener, thereby immobilizing the neck and head of the patient on the support from lateral or longitudinal movement. Additionally, a forehead band can be placed over the forehead of the patient, and attached to the end portions of the U-shaped head with a fourth fastener, thereby further restraining the head of the patient. A tension strap, attached to the base where the headband is attached to the base, can be placed under tension and secured to the support to provide traction to the head and neck of the patient. The fastener can comprise complementary hook-and-loop interlocking fabric pieces. The base can be attached to the support by elastic strips having hooks on their ends, which strips are affixed to the base.

25 Claims, 5 Drawing Figures

CERVICAL IMMOBILIZER

BACKGROUND OF THE INVENTION

The present invention relates to emergency medical equipment and, more specifically, to a cervical immobilizer for immobilizing a patient's head and neck when cervical injuries are suspected.

The present invention finds use as a device for immobilizing the head and neck of a patient. It is used primarily in emergency rescue where spinal and/or cervical injuries are known to be presented or are suspected. For example, the present invention can be used in emergency rescue activities in auto accidents, rough terrain rescue or during emergency service for any type of accident that requires the immobilization of the head and cervical column for transport of the patient to the nearest medical facility.

The present invention can also be used beyond the transporting phase of the rescue. For example, it can maintain the head and/or neck in immobilization while the patient is being X-rayed at the medical facility. The present invention is particularly designed to be X-ray permeable.

During the rescue of patients with known or suspected spinal or cervical injuries, the known methods of immobilizing the head and neck of the patient either involve placing sandbags alongside the head or neck of the patient, or taping the patient to a backboard, stretcher or other rigid support. These known methods are awkward and time-consuming. Additionally, the materials which are generally used in the known methods are not reuseable. It takes special handling of the patient when sandbags are used, since the stretcher or rigid support cannot be tilted very far from horizontal. This presents a major problem in air-lifting patients.

The present invention is designed to be utilized by land or air ambulance services, by hospitals, by fire stations/rescue squads, by search and rescue teams, or any other personnel during emergency medical rescue work.

Several devices are known in the art for restraining various portions of a patient's head or neck. For example, U.S. Pat. No. 1,487,628 shows a device for bandaging and restraining tissue for use in connection with the reformation of facial features, such as the nose, chin and ears. This device does not immobilize the entire head or neck of the patient. U.S. Pat. No. 1,930,440 shows a device for supporting the weight of the head of a patient on his shoulders and applying an extension force to the cervical vertabrae. This device does not prevent the lateral turning movement of the head, and is difficult to apply, especially to a comatose patient during rescue operations. U.S. Pat. No. 3,572,329 shows a chin strap for orthodontic and cosmetic uses which does not restrain or immobilize the entire head and neck of a patient. U.S. Pat. No. 3,779,549 shows a device for holding a hockey player's chin upward so as to restrain downward freedom of movement of the player's head. However, sidewards movement of the head is not at all restrained. Additionally, this device would be very difficult to apply during a rescue operation, even if the patient was conscious.

U.S. Pat. No. 3,285,658 discloses a head supporting device for holding the head of a passenger up while sleeping on a trip. While this device does restrain a head from moving, it requires that a person be in the upright sitting position, and that a seatback be available for the strap to be hung from. U.S. Pat. No. 3,548,816 shows an orthopedic traction device for applying cervical traction to a patient. This device also requires many further members to apply the force to the patient's head. It is impractical for rescue operations.

U.S. Pat. No. 3,397,688 discloses a pneumatic head and neck immobilizer, the device consisting of a helmet or hood enveloping a patient's head which has inflatable portions adapted to contact areas of the head when inflated. It further includes a means for holding the helmet on the head during inflation consisting of a harness passing around the armpits of the patient. This device has not proved practical for use in field rescue operations. It can easily be punctured during use, thereby eliminating any beneficial effect. While the device is being inflated, the possibility of compression of the cervical vertabrae exists which could be further damaging or injurious to the patient.

OBJECTS AND SUMMARY OF THE INVENTION

It is an object of the present invention to provide a method and an apparatus for immobilizing the head of a patient.

It is another object of the present invention to provide a method and apparatus for applying traction to the head and neck of a patient, while the head and neck is being held immobilized.

It is a further object of the present invention to provide a cervical immobilizer which is simple to use and effective in immobilizing the head and neck of a patient.

It is a still further object of the present invention to provide a cervical immobilizer which is simple and easy to manufacture and which can be simply and easily used in automobile accidents, rough terrain rescue or any type of accident that requires the immobilization of the head and cervical column for transport of the patient to the nearest medical facility.

The present invention is a cervical immobilizer for immobilizing the head of a patient on a support. The support, used hereinafter, refers to those typical rigid structures used by persons in rescue work such as long backboards, orthopedic spinal stretchers, short backboards, ambulance or air ambulance stretchers and the like.

The cervical immobilizer of the present invention comprises a base, a U-shaped head band having a center portion and two end portions attached to the base at the center portion, a first and a second cushion, with the first cushion being attached to one of the end portions of the head band and the second cushion being attached to the other, a means for attaching the base to the support, first cooperating means for fastening the first cushion to the base in varying positions, second cooperating means for fastening the second cushion to the base in varying positions, means for holding the chin of a patient in a fixed position, and third cooperating means for fastening the means for holding to the end portions of the headband in varying positions.

The cervical immobilizer can further comprise a tension means attached to the base for applying traction to the patient after immobilization with fourth cooperating means for fastening the tension means to itself when the tension means is engaged with the support.

The cervical immobilizer can further comprise a forehead band and fifth cooperating means for fastening the forehead band to the end portions of the headband.

The cervical immobilizer can further comprise means for stiffening the base to enable the base to be slipped between the patient and the support.

The means for attaching the base to the support can comprise elastic strips affixed to the base, together with means for engaging the support attached to the strips. Preferably, the means for engaging the support comprise hooks. The elastic strips can be any conventional elastic material, and are generally affixed to the base near each end thereof.

The cooperating means for fastening noted hereinabove preferably comprise complementary hook-and-loop interlocking fabric pieces. These fabric pieces as such are well-known to the art as "Velcro" and are described in U.S. Pat. Nos. 2,717,437 and 3,009,235. When a pair of such pieces of fabric are in face-to-face juxtaposition, the interlocking naps act to join them together. Microscopically, the interlocking naps appear to be hooks and loops. By applying sufficient force perpendicular to their surfaces, the pieces of fabric may be pulled apart. In the present application, whenever a particular means for fastening is referred to, it is understood that two complementary pieces Velcro fabric are intended. These enable the various elements of the invention to be positioned and secured in varying positions, depending upon the size of the patient being treated.

The present invention also includes a method of immobilizing the head and neck of a patient on a support comprising sliding a base between the patient and a support until a center portion of a U-shaped head band affixed to the base abuts the top of the head of the patient, attaching the base to the support, positioning a first cushion attached to a neck portion of the head band next to, and in contact with, one side of the head of the patient, securing the first cushion in position to the base with a first fastening means, positioning a second cushion attached to the other end portion of the head band next to, and in contact with, the other side of the head of the patient, securing the second cushion in position to the base with a second fastening means such that the central portion of the U-shaped headband is snug against the top of the head of the patient, and securing a chin strap cradling the chin of the patient by attaching the strap to the end portions of the U-shaped headband with a third fastening means, thereby immobilizing the neck and head of the patient on the support from lateral or longitudinal movement.

The present inventive method can further comprise securing a forehead band over the forehead of the patient by attaching the band to the two end portions of the U-shaped headband with a fourth fastening means, thereby further restraining the head of the patient.

The present inventive method can further comprise securing a tension strap under tension to the support, the tension strap being affixed to the base where the headband is attached at the center portion, thereby putting the head and neck of the patient into traction.

The cushions, the U-shaped head band, and the base can be made from a synthetic leather-like material, such as Naugahyde. The forehead band, the chin strap and the tension strap can be made from nylon webbing, leather or the like. The cushions can be filled with foam rubber.

When the base is made from a flexible material, such as the synthetic leather-like material noted above, a certain amount of stiffening is necessary to be able to easily slide the base between the patient and the support. Thus, the present invention can further comprise pockets made within the base having stiffening means therein. The stiffening means can comprise plastic, wood, metal or the like. Plastic or wood are preferred since these materials are X-ray permeable. Due consideration should be given in selecting materials for the construction of the cervical immobilizer of the present invention, so that all of the materials are X-ray permeable to allow the device to be used for restraining or immobilizing the head and neck of the patient while undergoing X-ray testing at a medical facility or other place.

BRIEF DESCRIPTION OF THE DRAWINGS

The above and other objects, and the attendant advantages of the present invention will become readily apparent by reference to the following detailed description when considered in conjunction with the accompanying drawings wherein.

Like reference characters refer to like parts throughout the several views of the drawings.

DETAILED DESCRIPTION OF PREFERRED EMBODIMENTS

Figure 1:
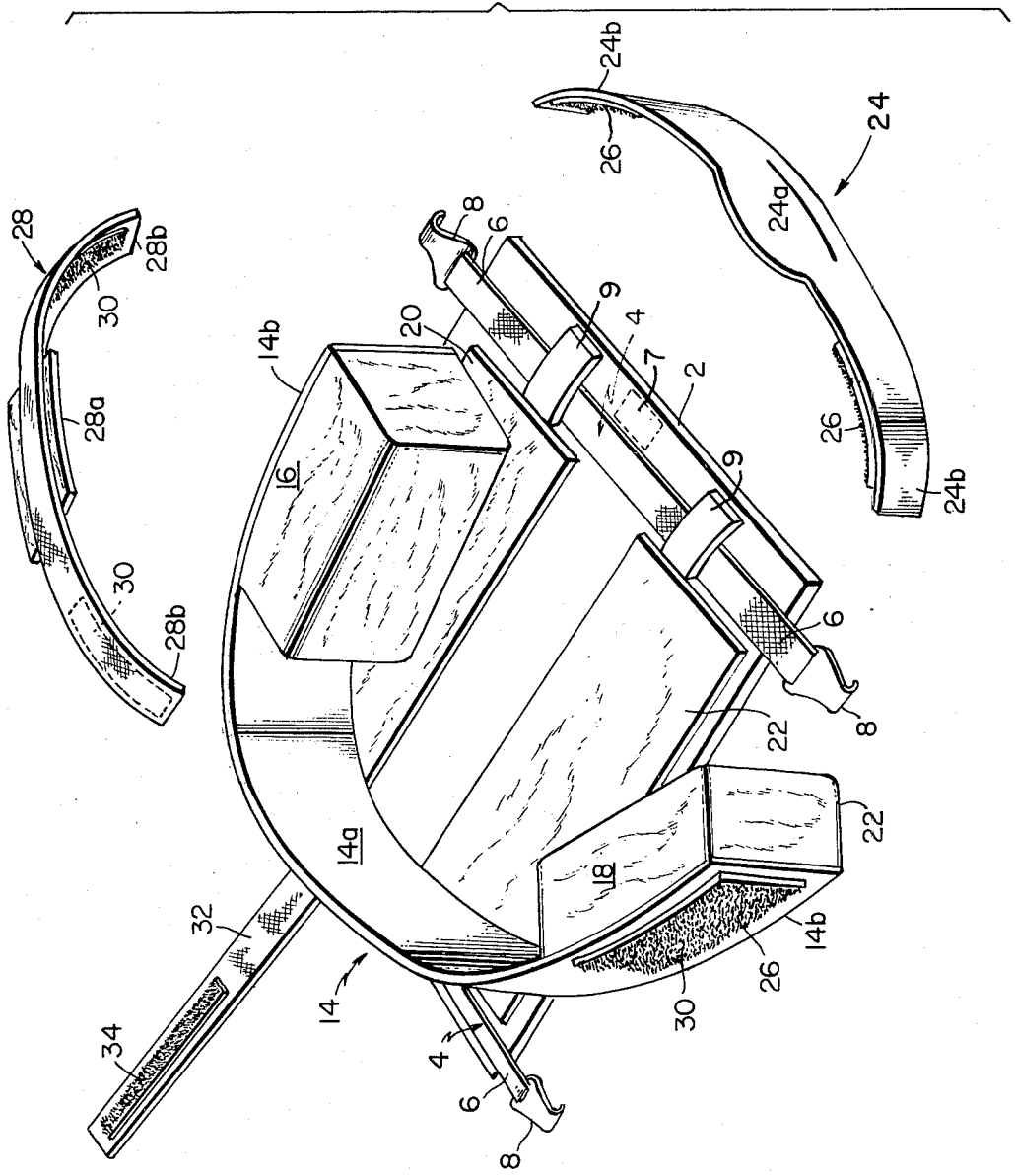
FIG. 1 is an exploded, isometric view of the present invention.

FIG. 1 shows an exploded, perspective view of the present invention which comprises a base 2 having an attachment means 4 thereon for attaching the base 2 to a support 12. The support 12 can be seen clearly in FIGS. 2 and 4.

The attachment means 4 can comprise elastic strips 6 having a means 8 for engaging the support 12. The means 8 for engaging the support 12 can be simple hooks. The elastic strips 6 are generally affixed to the base 2 at center thereof as at 7; passing through two webbing keepers 9 on each side.

A U-shaped headband 14 is attached to the base 2. The U-shaped headband 14 has a central portion 14a and end portions 14b. Generally, the headband 14 is affixed to the base 2 at its lower edge at the center portion 14a. The headband 14 is made of a flexible material which, for example, can be a synthetic leather-like material.

A first cushion 16 and a second cushion 18 are attached to the end portions 14b of the headband 14. The cushions 16,18 can also be made of a synthetic leather-like material and can be filled or stuffed with foam rubber or the like.

Figure 2:
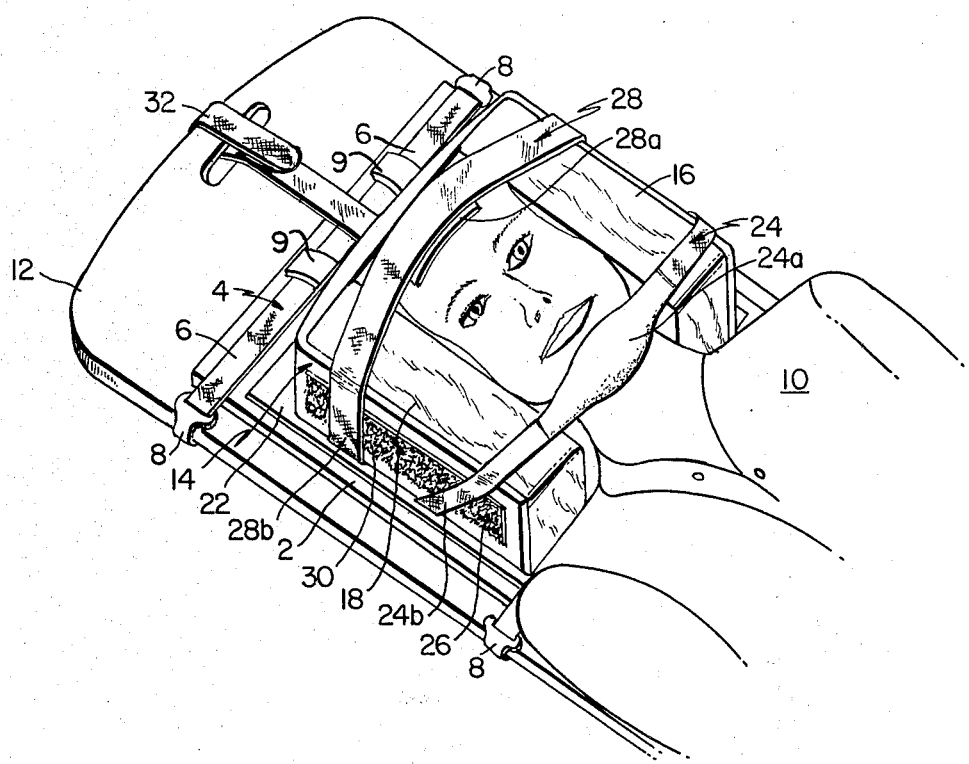
FIG. 2 is an isometric view of the present invention in use with a patient on a support.

First cooperating means 20 are provided for fastening the first cushion 16 to the base 2 in varying positions. The cooperating means 20 comprises two pieces of complementary hook-and-loop interlocking fabric pieces, generally known in the art as "Velcro". One piece is affixed to the bottom of the first cushion 16, and the other piece is affixed to the tray 2. This can be most clearly seen in FIG. 5. This enables the variable positioning of the first cushion such that it is next to, and in contact with, one side of the head of the patient as can be seen in FIG. 2. Variable positioning of the cushions is a great advantage of the present invention, since patients are not exactly uniform in size.

Second cooperating means 22 for fastening the second cushion 18 to the base 2 in varying positions can be constructed identically with first cooperating means 20. Namely, two pieces of Velcro can be provided, one affixed to the bottom of the second cushion 18 and the other affixed to the top surface of the base 2.

Figure 5:
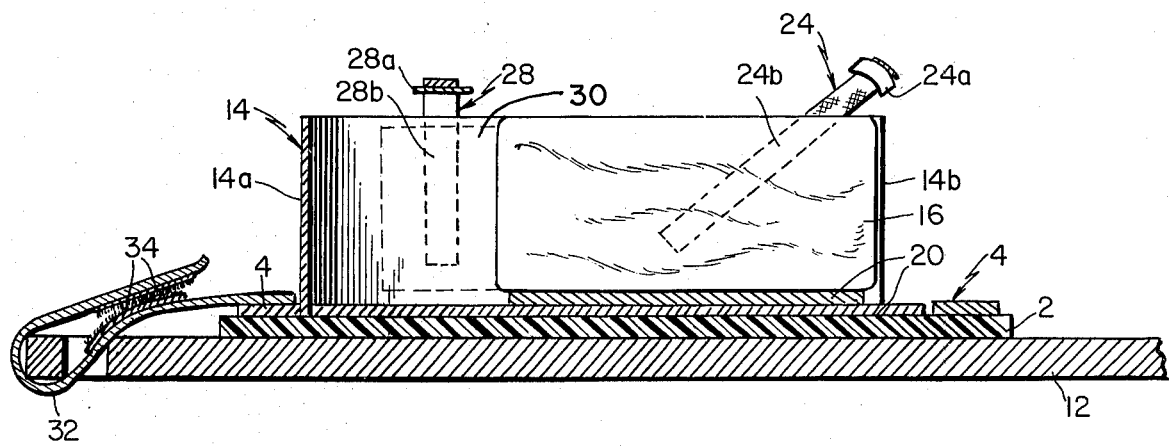
FIG. 5 is a cross-sectional view taken along lines V—V of FIG. 4.
Figure 3:
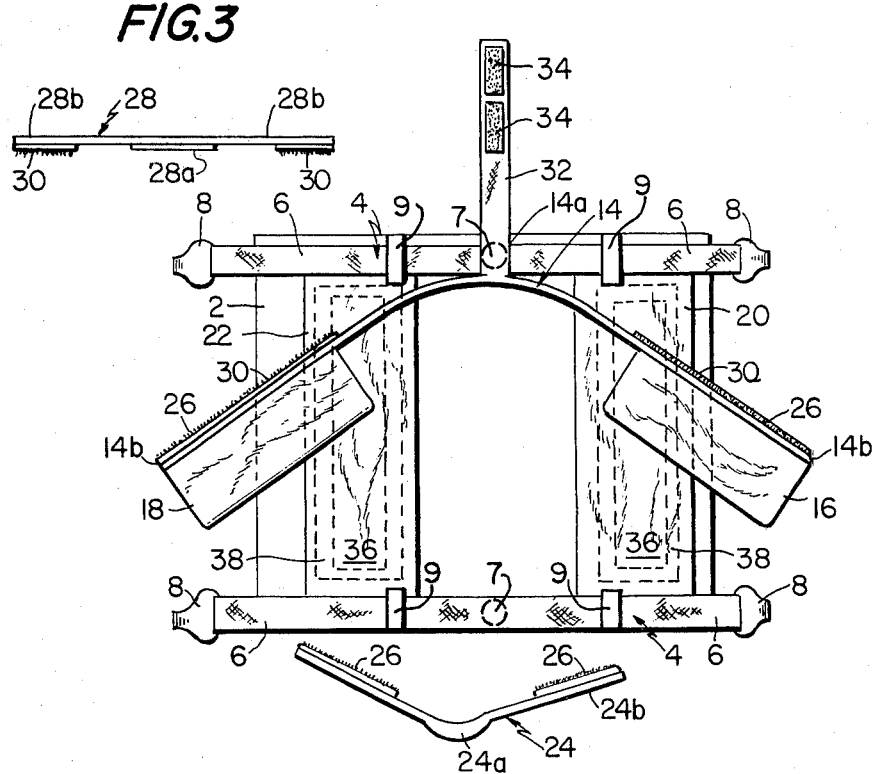
FIG. 3 is a plan view of the present invention prepared for use.
Figure 4:
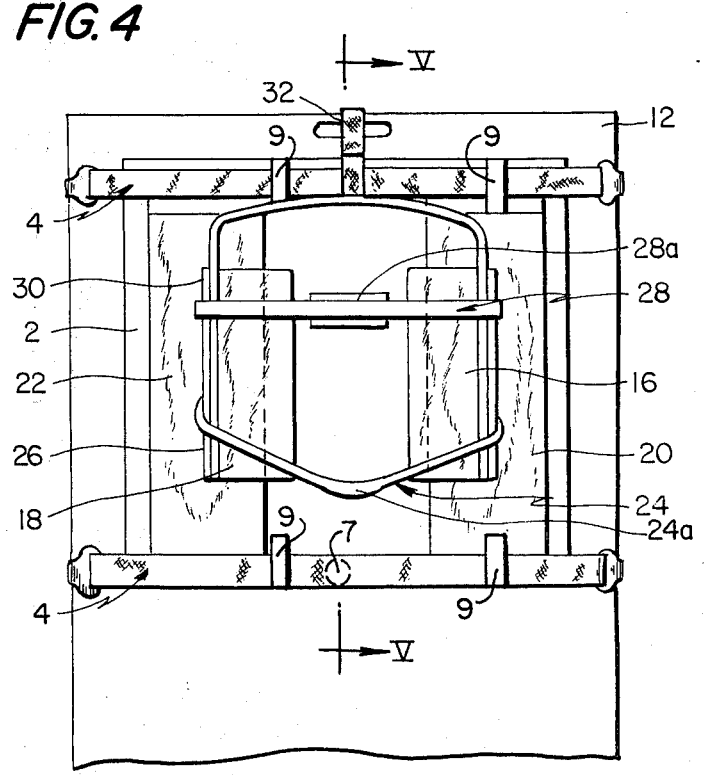
FIG. 4 is a plan view of the present invention in use.

Means 24 for holding the chin of the patient in a fixed position can be seen in the exploded views of FIGS. 1 and 3, and in position for use in FIGS. 2, 4 and 5. The means 24 can comprise a chin strap having a chin cup 24a and strap ends 24b for holding the chin of a patient in a fixed position as can be clearly seen in FIG. 2. The chin cup 24a can be made of leather, plastic and the like. The chin strap can be made of nylon webbing, leather and the like. The chin strap 24 can be positioned relatively vertically to the head of the patient, or relatively horizontally to the head of the patient, so that the trachea can be kept open.

Third cooperating fastening means 26 are provided for fastening the means 24 for holding the chin to the end portions 14b of the headband 14 in varying positions. Similarly to the cooperating means 20 and 22, most preferably, the cooperating means 26 also comprise complementary hook-and-loop interlocking fabric pieces, such as Velcro. One such piece can be placed on the outer surface of the end portion 14b of the headband 14, while the other is placed on the two chin straps 24b so that the chin strap 24 can be placed in varying positions.

Tension means 32 is attached to the base 2 for applying traction to the patient after immobilization, as can be most readily seen in FIGS. 2, 4 and 5. The tension means 32 can comprise a tension strap having an end portion, and is preferably affixed to the base 2 near where the headband 14 is attached. The end portion of the tension strap 32 has opposite sides, with the fourth cooperating means 34 for fastening the tension strap 32 to itself. In use, after the patient's head and neck are immobilized, the tension strap 32 is pulled towards the end of the support 12 and looped through a portion thereof, and attached to itself utilizing the fourth cooperating means 34.

Fourth cooperating means 34 can comprise complementary hook-and-loop interlocking fabric pieces, such as Velcro. The tension strap 32 can be made by nylon webbing, leather and the like.

A forehead band 28 can be provided having thereon a forehead pad 28a. The forehead band 28 has ends 28b. The forehead band 28 can be made of leather, nylon webbing and the like.

The forehead band 28 is fastened in variable positions to the outer surfaces of the end portions 14b of the headband 14 by fifth cooperating means 30. Fifth cooperating means 30 can comprise complementary hook-and-loop interlocking fabric pieces, such as Velcro. One such piece would be attached on the inside surface portion of the end 28b and the other piece would be attached to the outside surface of the end portion 14b of the headband 14. Thus, as can be seen in FIGS. 2 and 4, the forehead band 28 can be fastened to the present invention to further restrain the head of the patient 10.

In the case where the base 2 is made of a flexible material such as a synthetic leather-like material, stiffening means are preferable to enable the easy manipulation of the base 2 between the patient 10 and the support 12. The stiffening means can comprise stiffeners 36 slide and held in pockets 38 internal or integral with the base 2. The stiffeners 36 can be made of plastic, metal, wood or the like. Wood or plastic are preferred since these substances are X-ray permeable.

The present invention also comprises a method of immobilizing a head and neck of a patient 10 on a support 12 which comprises sliding a base 2 between the patient 10 and the support 12, until a center portion 14a of a U-shaped headband 14 affixed to the base 2 abuts the top of the patient 10. The base 2 is then attached to the support 12 utilizing attachment means 4. The first cushion 16 attached to the end portion 14b of headband 14 is positioned next to, and in contact with, one side of the head of the patient 10. The first cushion 16 is then secured to the base 2 with the first fastening means 20.

The second cushion 18 attached to the other end portion 14b of the headband 14 is positioned next to, and in contact with, the other side of the head of the patient 10. The second cushion 18 is secured to the base 2 by the second fastening means 22 such that the central portion 14a of the U-shaped headband 14 is snug against the top of the head of the patient 10. The chin strap 24 cradling the chin of the patient is then attached to the end portions 14b of the U-shaped headband 14 with the third fastening means 26. The neck and head of the patient are thereby immobilized from lateral or longitudinal movement, as can be seen in FIG. 2.

The forehead band 28 can be positioned over the forehead of the patient 10 and thereafter attached to the end portions 14b of the U-shaped headband 14 with the fourth fastening means 30, thereby further restraining the head of the patient.

A tension strap 32 affixed to the base 2 where the headband 14 is attached at the center portion 14a can be placed under tension and secured to the support 12 by looping the strap 32 through a part of the support 12 and fastening it to itself utilizing fifth cooperating means 34. Thus, the head and neck of the immobilized patient can be thereby placed into traction.

It is readily apparent that the above-described cervical immobilizer and method meet all of the objects mentioned and also have the advantage of wide utility in rescue operations. It should be understood that the specific form of the invention hereinabove described is intended to be representative only, as certain modifications within the scope of these teachings will be apparent to those skilled in the art of emergency rescue equipment.

Accordingly, reference should be made to the following claims in determining the full scope of the invention.

What is claimed:

1. A cervical immobilizer for immobilizing a head of a patient on a support comprising:
   a base;
   a U-shaped headband having a center portion and two end portions attached to said base at said center portion;
   a first and second cushion, said first cushion being attached to one of said end portions and said second cushion being attached to the other;
   means for attaching said base to the support;
   first cooperating means for fastening said first cushion to said base in varying positions;
   second cooperating means for fastening said second cushion to said base in varying positions;
   means for holding the chin of the patient in a fixed position; and third cooperating means for fastening said means for holding to said end portions in varying positions.

2. A cervical immobilizer according to claim 1 further comprising tension means attached to said base for applying traction to the patient after immobilization, and fourth cooperating means for fastening said tension means to itself when said tension means is engaged with the support.

3. A cervical immobilizer according to claim 1 further comprising a forehead band and fifth cooperating means for fastening said forehead band to said end portions.

4. A cervical immobilizer according to claim 1 further comprising means for stiffening said base to enable said base to be slipped between the patient and the support.

5. A cervical immobilizer according to claim 1 wherein said means for attaching comprises elastic strips affixed to said base and means for engaging the support attached to said strips.

6. A cervical immobilizer according to claim 5 wherein said means for engaging comprises hooks.

7. A cervical immobilizer according to claim 1 wherein said first, second and third cooperating means for fastening comprise complementary hook-and-loop interlocking fabric pieces.

8. A certical immobilizer according to claim 2 wherein said fourth cooperating fastening means comprises complementary hook-and-loop interlocking fabric pieces.

9. A cervical immobilizer according to claim 3 wherein said fifth cooperating fastening means comprises complementary hook-and-loop interlocking fabric pieces.

10. A cervical immobilizer for immobilizing a head of a patient on a support comprising:
a base;
a U-shaped head band having a center portion and two end portions attached to said base at said center portion;
a first and a second cushion, said first cushion being attached to one of said end portions and said second cushion being attached to the other;
means for attaching said base to the support;
first cooperating means for fastening said first cushion to said base in varying portions;
second cooperating means for fastening said second cushion to said base in varying positions;
means for holding the chin of the patient in a fixed position;
third cooperating means for fastening said means for holding to said end portions in varying positions;
tension means attached to said base for applying traction to the patient after immobilization;
fourth cooperating means for fastening said tension means to itself when said tension means is engaged with the support;
a forehead band; and
fifth cooperating means for fastening said forehead band to said end portions.

11. A cervical immobilizer according to claim 10 wherein said means for attaching comprises elastic strips affixed to said base and means for engaging the support attached to said strips.

12. A cervical immobilizer according to claim 11 wherein said means for engaging comprises hooks.

13. A cervical immobilizer according to claim 10 wherein said first, second, third, fourth and fifth cooperating means for fastening comprise complementary hook-and-loop interlocking fabric pieces.

14. A cervical immobilizer for immobilizing a head of a patient on a support comprising:
a base having two ends, two sides and a top surface;
a U-shaped headband having an edge, a center portion, and two end portions, each end portion having an inner surface and an outer surface, said headband being attached on said edge at said enter portion to one end of said base;
a first and second cushion, each having a top, a bottom, an outer surface and an inner surface, said first cushion being affixed on its outer surface to said inner surface of one end portion of said headband and said second cushion on its outer surface to said inner surface of the other end of said headband;
means for attaching said base to the support, said means for attaching being affixed to said base near said ends of said base;
first cooperating fastening means affixed to said bottom of said first cushion and said top surface of said base for fastening in variable positions said first cushion to said base;
second cooperating fastening means affixed to said bottom of said second cushion and said top surface of said tray base for fastening in variable positions said second cushion to said base;
a chin strap having a chin cup and strap ends for holding the chin of the patient in a fixed position; and
third cooperating fastening means for fastening in variable positions said strap ends to said outer surfaces of said end portions of said headband.

15. A cervical immobilizer according to claim 14 further comprising a tension strap having an end portion and being affixed to said base near where said headband is attached for applying traction to the patient after immobilization, said end portion of said tension strap having opposite sides with a fourth cooperating fastening means affixed thereto whereby said tension strap can be looped around part of the support and affixed to itself to apply traction to the patient.

16. A cervical immobilizer according to claim 14 further comprising a forehead band having a forehead pad and two ends for restraining the forehead of the patient and fifth cooperating fastening means for fastening in variable positions said ends of said forehead band to said outer surfaces of said end portions of said headband.

17. A cervical immobilizer according to claim 14 wherein said base has two internal pockets arranged from end to end, further comprising means in said pockets for stiffening said base to enable said base to be slipped between the patient and the support.

18. A cervical immobilizer according to claim 14 wherein said means for attaching comprises means for engaging the support and elastic strips having opposite ends with one end of each strip being affixed to said base near one of said ends of said base and the opposite end of each strip carrying said means for engaging whereby when said elastic strips are stretched and said means for engaging are engaged to the support, said base is securely attached to the support.

19. A cervical immobilizer according to claim 18 wherein said means for engaging comprise hooks.

20. A cervical immobilizer according to claim 14 wherein said first, second and third cooperating means for fastening comprise complementary hook-and-loop interlocking fabric pieces.

21. A cervical immobilizer according to claim 15 wherein said fourth cooperating fastening means comprises complementary hook-and-loop interlocking fabric pieces.

22. A cervical immobilizer according to claim 16 wherein said fifth cooperating fastening means comprises complementary hook-and-loop interlocking fabric pieces.

23. A method of immobilizing a head and neck of a patient on a support comprising:
   sliding a base between the patient and the support until a center portion of a U-shaped headband affixed to said base abuts the top of the head of the patient;
   attaching said base to the support;
   positioning a first cushion attached to an end portion of said headband next to and in contact with one side of the head of the patient;
   securing said first cushion in position to said base with a first fastening means;
   positioning a second cushion attached to the other end portion of said headband next to, and in contact with, the other side of the head;
   securing said second cushion in position to said base with a second fastening means such that said central portion of said U-shaped headband is snug against the top of the head; and
   securing a chin strap cradling the chin of the patient by attaching said strap to said end portions of said U-shaped headband with a third fastening means, thereby immobilizing the neck and head of the patient on the support from lateral or longitudinal movement.

24. A method according to claim 23 further comprising securing a forehead band over the forehead of the patient by attaching said band to said end portions of said U-shaped headband with a fourth fastening means, thereby further restraining the head of the patient.

25. A method according to either claim 23 or claim 24 further comprising securing a tension strap under tension to the support, said tension strap being affixed to said base where said headband is attached at said center portion, thereby putting the head and neck of the patient into traction.

* * * * *